United States Patent [19]

Kaster

[11] 3,996,623
[45] Dec. 14, 1976

[54] METHOD OF IMPLANTING A PROSTHETIC DEVICE AND SUTURING MEMBER THEREFOR

[76] Inventor: Robert L. Kaster, 2730 Vagabond Lane, Wayzata, Minn. 55391

[22] Filed: June 30, 1975

[21] Appl. No.: 591,428

Related U.S. Application Data

[63] Continuation of Ser. No. 493,027, July 30, 1974, abandoned.

[52] U.S. Cl. .......................................... 3/1.5; 3/1; 128/334 R
[51] Int. Cl.² ...................... A61F 1/22; A61F 1/00
[58] Field of Search ................ 3/1, 1.5; 128/334 R, 128/334 C, 335

[56] References Cited
UNITED STATES PATENTS

| | | | |
|---|---|---|---|
| 3,099,016 | 7/1963 | Edwards | 3/1.5 |
| 3,263,239 | 8/1966 | Edwards et al. | 3/1.5 |
| 3,402,710 | 9/1968 | Paleschuck | 3/1 X |
| 3,463,158 | 8/1969 | Schmitt et al. | 128/334 R |
| 3,503,079 | 3/1970 | Smith | 3/1.5 |
| 3,725,961 | 4/1973 | Magovern et al. | 3/1.5 |
| 3,737,919 | 6/1973 | Child | 3/1.5 |
| 3,763,548 | 10/1973 | Anderson | 3/1 X |

Primary Examiner—Ronald L. Frinks
Attorney, Agent, or Firm—Burd, Braddock & Bartz

[57] ABSTRACT

An annular sewing member mounted on the base of a heart valve and attached to heart tissue with sutures. The sewing member has spaced outwardly directed flanges connected with a body forming a central annular outwardly open groove adapted to accommodate heart tissue after the natural heart valve has been removed. The flanges are relatively thin and contain an internal core of cured plastic, as Silastic. The flanges can be fabric without an internal core. A heat shrunk collar or sleeve surrounded with cord retains the suturing member in movable assembled relation with the base of the heart valve to permit angular orientation of the valving member of the valve. Stitches extend through one of the sewing member flanges and the heart tissue attaching the sewing member to the heart tissue. The knots of the stitches are located under the second flange, thereby protecting the knots and minimizing clots. The flange without knots form a smooth surface with a thin endothelium tissue layer. In another form, the stitches extend through both of the flanges to provide a stronger mechanical attachment of the sewing member to the heart tissue.

10 Claims, 5 Drawing Figures

U.S. Patent      Dec. 14, 1976      3,996,623
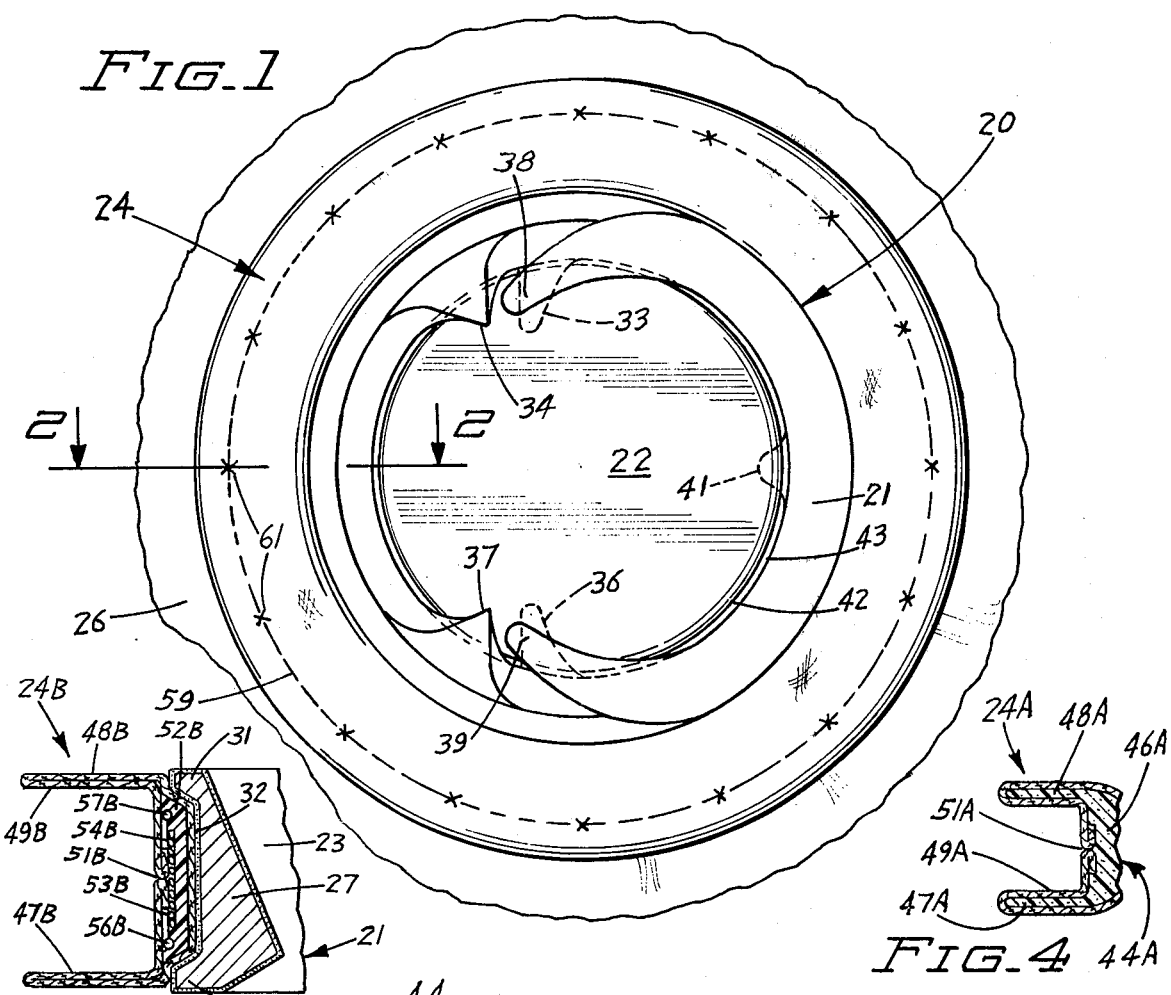
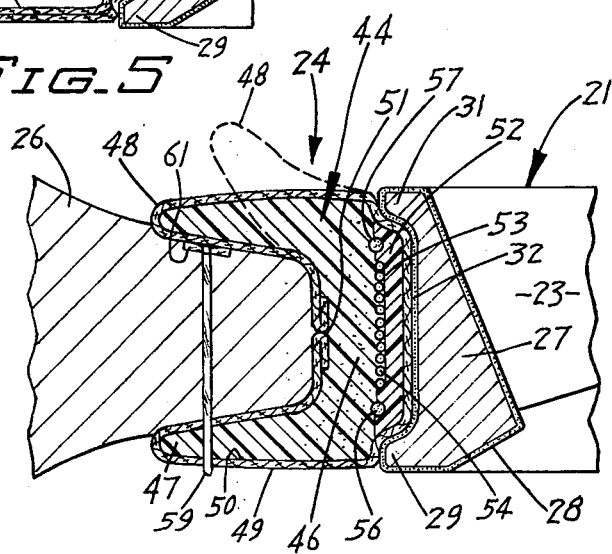
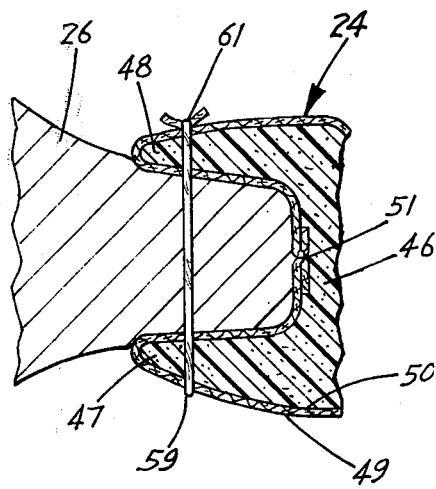

METHOD OF IMPLANTING A PROSTHETIC DEVICE AND SUTURING MEMBER THEREFOR

This is a continuation of application Ser. No. 493,027, filed July 30, 1974 and now abandoned.

BACKGROUND OF THE INVENTION

Suturing members or sewing rings are commonly used to accommodate sutures used to attach prostheses, as heart valves, to tissue. The suturing member is made of biologically inert material that is relatively compatible with blood and intracardiac tissue and has structure which does not inhibit tissue ingrowth into the suturing member.

A clamp ring and wire is disclosed in U.S. Pat. No. 3,099,016 to hold the suturing member on the valve base. A stainless steel ring encased in porous material is used in U.S. Pat. No. 3,396,409 to hold the porous material on the base of the heart valve. Child, in U.S. Pat. No. 3,623,212, discloses a suturing member for implantable devices and the method of making the suturing member on the device. The cover is held on the valve base with a plurality of cords or threads. The sewing member has a single annular flange adapted to accommodate the sutures used to attach the suturing member to the heart tissue. Single annular flanges can only be located in a supra-annular position or a sub-annular position.

SUMMARY OF THE INVENTION

The invention relates to a suturing member for connecting an implantable prosthesis, as a heart valve, to tissue. The suturing member has a plurality of outwardly directed annular flanges adapted to be located on opposite sides of the heart tissue surrounding the valve opening in the heart. The flanges extend outwardly from an annular base mounted on the outer side wall of a heart valve. A heat shrunk collar can be used to hold the suturing member on the base of the heart valve. Stitches are used to attach one of the flanges to the heart tissue. The knots of these stitches are located on top of annular tissue and under the second flange. The stitches can extend through both of the flanges to provide a stronger mechanical attachment of the suturing member to the heart tissue. The suturing member locates the valve at the level of the midpoint of the annulus formed by removing the natural heart valve.

It is an object of the invention to provide a suturing member which locates the heart valve at the midpoint of the annulus of the opening in the tissue of the heart. Another object of the invention is to provide a suturing member with a flange which covers the knots and ends of the sutures used to attach the suturing member to the heart tissue. A further object of the invention is to provide a suturing member which can be used to provide a suturing member which can be used to provide a strong mechanical clamping connection to the heart tissue. A still further object of the invention is to provide a suturing member with a seam that is covered by the heart tissue.

IN THE DRAWINGS

FIG. 1 is a top plan view of a heart valve mounted in assembled relation with a suturing member with the suturing member attached to heart tissue;

FIG. 2 is an enlarged sectional view taken along the line 2—2 of FIG. 1 showing stitches extended through one of the flanges and the annular heart tissue with the suture knots tied against the heart tissue and covered by the second flange;

FIG. 3 is a view similar to FIG. 2 showing the sutures extended through both of the flanges of the suturing member and the annular heart tissue;

FIG. 4 is a sectional view of the flanges of a modified suturing member; and

FIG. 5 is a sectional view similar to FIG. 2 of another modified suturing member.

DESCRIPTION OF THE PREFERRED EMBODIMENT

Referring to the drawings, there is shown in FIG. 1 a heart valve indicated generally at 20. Valve 20 is a pivoting disc heart valve and follows the valve structure shown in U.S. Pat. Nos. 3,476,143 and No. 3,737,919. This valve is illustrated only by way of example as other types of heart valves and other implantable protheses can utilize the suturing member of the invention.

Valve 20 has an annular base 21 cooperating with a valving member or occluder 22 for controlling the flow of blood through a passage 23 to the base 21. A suturing member or sewing cuff indicated generally at 24 is located around base 21 and attached to the heart tissue 26 with sutures 59.

Base 21 is a one-piece member having a core 27 of material as graphite, metal, plastic or the like, and an external coat or layer 28. Layer 28 is preferably silicone alloyed Pyrolytic carbon or other thrombo-resistant materials. An example of this material is disclosed in U.S. Pat. No. 3,737,919. Base 21 has an outwardly directed proximal annular flange 29 and an outwardly directed distal annular flange 31. An annular outwardly open groove 32 is located between flanges 29 and 31. The suturing member 24 is located in the groove 32 and retained therein in a manner which permits rotation of the valve base 21 relative to the suturing member to orient the valving member 22. Suturing member 24 can be used with implantable prostheses other than heart valves. The following description, directed to a suturing member on a heart valve, is an example of one use of the suturing member of the invention.

Referring to FIG. 1, base 21 has a first pair of pivot members 33 and 34 projected inwardly into the valve opening. Circumferentially spaced from the first pair of members are a second pair of pivot members 36 and 37 projected into the valve opening 23. Each pair of pivot members has a proximal member and a distal member located on opposite sides of valving member 22. The pairs of pivot members 33, 34, 36, and 37 cooperate with a pair of upwardly directed projections or elements 38 and 39 for controlling the pivotal action of the valving member 22. The valving member 22 is a generally flat circular disc having an annular outer uninterrupted peripheral edge 42. When the valving member 22 is in the closed position, it rests on an inwardly directed stop 41 attached to the inner wall of the base 21 and on proximal pivot member 33 and 36. The annular outer peripheral edge 42 is spaced a slight distance 43 away from the inner wall of the base to permit limited reverse flow of blood through the valve passage 23 when the disc 22 is in the closed position.

The suturing member 24 has an annular core indicated generally at 44 of synthetic material, as Silastic. Core 44 has a cylindrical part or body 46 and outwardly directed annular flanges 47 and 48. Core 44 is a pliable plastic in the uncured state which is compatible with the human tissue and body fluids. In addition, core 44 is sterilizable, biologically inert, non-irritating, non-pyrogenic and non-toxic to body fluids and tissue. On curing of the plastic core 44 with heat, a bond 50 is achieved between the inside surface of the cover 40 and the plastic core to eliminate all pockets or separations of the cover 49 from the core 44 which could collect fluids. The core 44 preferably is a plastic, such as Dow "Silastic", fluorosilicone rubber or a similar synthetic resinous plastic material. Proximal annular flange 47 extends from the opposite side of the base 46. Flanges 47 and 48 have uniform thickness throughout their encircling annular extent and extend and taper radially outwardly generally the same distance. The base 46 and flanges 47 and 48 are covered with a fabric cover 49, such as "Teflon" or "Dacron" cloth. The ends of the cover 49 are attached with stitches or seam 51 located in the center portion of the base between flanges 47 and 48. The material of the cover 49 is biologically inert and does not deteriorate with time. The material preferably is an interlaced or knitted fabric having spaces into which living neointima tissue grows to form a permanent mechanical union between the suturing member and the neointima tissue independent of the sutures applied by the surgeon.

Positioned within cover 49 adjacent the valve base 21 is a heat shrunk collar or sleeve 52. Sleeve 52 has an outwardly open groove 53 accommodating a plurality of cords or threads 54. A groove in the proximal end of sleeve 52 accommodates a cord 56. In a similar manner, the distal end of sleeve 52 accommodates a cord 57. The outer surface of the core 44 is attached to the inner surface of the fabric with a bond 50 in the process of manufacturing the suturing member. The process of maufacturing the suturing member and mounting the suturing member on the valve base is disclosed in co-pending U.S. patent application Ser. No. 279,936, now U.S. Pat. No. 3,781,969. The core 44 can be precured and placed around the sleeve 52. Cover 49 can be placed around the cured core and connected with seam or stitches 51. The precured core does not bond to the cover.

The suturing member 24 is attached to the heart tissue 26 with a plurality of stitches 59. The stitches 59 extend circumferentially around the suturing member 24 and have knots 61. As shown in FIG. 2, the stitches are located through flange 47 and through the heart tissue 26. The knots and ends 61 of the stitches 59 are covered with the flange 48. During tying of the sutures 59, the flange 48 is moved and held away from the heart tissue, as shown in broken lines, until all of the sutures are tied. The flange 48 is then released so that it can return to its position covering the ends and knots 61. The flange 48 protects the knots and ends and minimizes clots. The outer surfaces of flanges 47 and 48 are relatively smooth and in time endothelize with thin tissue layers. The heart tissue in time will grow into the fabric cover to permanently enclose the knots and ends 61 as well as the seam 51.

Referring to FIG. 3, the sutures 59 extend through both flanges 47 and 48 and the heart tissue between the flanges. In cases where the heart tissue is weak and does not support the knots and ties, the surgeon can stitch through both of the flanges 47 and 48 to attach the suturing member to the heart tissue. This will enhance a stronger mechanical clamping attachment as well as two anchoring members for the suturing member. The heart tissue 26, being located in the groove between the flanges, will cover the seam 51.

Referring to FIG. 4, there is shown a suturing member 24A. The parts of suturing member 24A that correspond to suturing member 24 have the same reference numbers with the suffix A. Suturing member 24A has outwardly directed annular flanges 47A and 48A covered with a cloth cover 49A. The flanges 47A and 48A each have a thickness approximately equal to the thickness of the cloth cover 49A, thereby providing minimal elevation of the suturing member. The thickness of the core material and flanges can vary. The seam 51A is located in the midsection of the groove between the flanges 47A and 48A. A heat shrunk collar or sleeve (not shown) is used to hold the suturing member 24A on a base or body of an implantable prosthesis.

Referring to FIG. 5, there is shown a modified suturing member 24B mounted on a heart valve base 21. The parts of suturing member 24B that correspond to the parts of suturing member 24 are identified with same reference numbers having the suffix B. Suturing member 24B has flexible fabric flanges 47B and 48B formed by folding the fabric cover 49B. The ends of cover 49B are attached together with stitches or seam 51B. Seam 51B is located in the middle of the bottom or base of the annular U-shaped groove formed by the flanges 47B and 48B. Cover 49B is held on the outer wall of the valve base 21 with a heat shrunk annular collar or sleeve 52B. Sleeve 52B has an outwardly open annular groove 53B accommodating a plurality of cords or threads 54B. An annular groove in the proximal end of sleeve 52B holds a cord 56B. In a similar manner, the distal end of sleeve 52B holds a cord 57B. The heat shrunk sleeve 52B and cords 54B, 56B and 57B hold the cover 49B in movable assembled relation with base 21 so that the base can be rotated relative to the suturing member 24B after the suturing member is connected to the heart tissue. Suturing member 24B can be attached to the heart tissue in the manner shown in FIG. 2 or FIG. 3.

While there have been shown and described preferred embodiments of the suturing member and features of attaching the suturing member to the heart tissue, it is understood that modifications and alterations in the suturing member and procedure may be made by those skilled in the art without departing from the invention. For example, the suturing member can be attached to tissue other than heart tissue when used with other types of implantable prostheses.

The embodiments of the invention in which an exclusive property or privilege is claimed are defined as follows:

1. A method of implanting a heart valve on an annular portion of heart tissue surrounding an opening in the heart formed by the removal of a natural heart valve with a suturing member having a radial outwardly directed first annular flange and a radial outwardly directed second annular flange spaced from the first flange forming an annular groove between said flanges for accommodating the annular portion of the heart tissue comprising: positioning the valve carrying the suturing member in the opening in the heart at about the midpoint of the annulus of the opening, locating an annular portion of the heart tissue surrounding said opening in the annular groove between said first and second annular flanges, placing stitches in one of said flanges and the annular portion of the heart tissue, and tying said stitches adjacent the inside of the other of said flanges whereby said other flange covers the knots and ends of the tied stitches.

2. The method of claim 1 including: providing a plurality of stitches circumferentially in said one of said flanges of the suturing member and the annular portion of the heart tissue.

3. The method of claim 1 wherein: said heart valve is provided with a movable disc and the method further includes rotation of the valve base relative to the suturing member to orient the disc after the suturing member has been stitched to the heart tissue.

4. The method of claim 1 including: holding the other of said flanges away from the annular portion of the heart tissue during the placing of stitches in one of said flanges and annular portion of heart tissue and tying said stitches.

5. A method of implanting a prosthetic device on an annular portion of tissue surrounding an opening in a body with a suturing member having a radial outwardly directed first annular flange and a radial outwardly directed second annular flange spaced from the first flange forming an annular groove between said flanges for accommodating the annular portion of tissue comprising: positioning the device carrying the suturing member in the opening in the body at about the midpoint of the annulus of the opening, locating an annular portion of the tissue surrounding the opening in the annular groove between said first and second annular flanges, placing stitches in one of said flanges and the annular portion of the tissue, and tying said stitches adjacent the inside of the other of said flanges whereby said other flange covers the knots and ends of the tied stitches.

6. The method of claim 5 including: providing a plurality of stitches circumferentially in one of said flanges of the suturing member and the annular portion of the tissue.

7. The method of claim 5 including: holding the other of said flanges away from the annular portion of the tissue during placing of the stitches in one of said flanges and the annular portion of the tissue and tying said stitches.

8. A suturing member and heart valve adapted to be connected to an annular portion of heart tissue surrounding an opening formed by the removal of a natural heart valve comprising: a heart valve having a base with an inlet side, an outlet side, an outside wall and an inside wall surrounding a passage connecting the inlet side with the outlet side thereby allowing blood to flow through the base, said outside wall having a radial outwardly directed first annular flange adjacent the outlet side of the base and a radial outwardly directed second annular flange adjacent the inlet side of the base, an annular first groove located between said first and second flanges of the outside wall, valving means cooperating with the base to restrict the flow of blood in one direction through said passage, a suturing member surrounding and mounted on the outside wall of the base, said suturing member having a flexible plastic core, a fabric cover surrounding the core, and annular means surrounding an annular portion of the cover to hold the suturing member on the outside wall of the base, said core and cover having an annular body, a radial outwardly directed first annular flexible flange extending outwardly from the body adjacent the outlet side of the base, said first annular flexible flange having an outer surface extended generally coextensive with the transverse plane of the outlet side of the base, a radial outwardly directed second annular flexible flange spaced from the first flexible flange and extended outwardly from the body adjacent the inlet side of the base, said second annular flexible flange having an outer surface extended generally coextensive with the transverse plane of the inlet side of the base, said first and second annular flexible flanges forming with the body an annular second groove between said first and second annular flexible flanges for accommodating the annular portion of the heart tissue surrounding the opening in the heart to locate the base at about the midpoint of the annulus of the opening, said cover having a connected seam extending around the base of the second groove, said first and second annular flexible flanges each having a radial outward taper and a radial length sufficient to extend adjacent opposite sides of the annular portion of the heart tissue to accommodate sutures for connecting at least one of said flanges to the annular portion of the heart tissue, said body having a radial thickness greater than the thickness of said first and second annular flexible flanges, said annular means holding the suturing member on the outside wall of the base including an annular member holding parts of the suturing member in engagement with the first and second annular flanges of the outside wall and a part of the suturing member in the annular first groove in the outside wall of the base whereby the first flexible flange of the suturing member and the second flexible flange of the suturing member are located between the transverse planes of the outlet side and inlet side of the base.

9. The structure of claim 8 wherein: the first annular flange and second annular flange of the suturing member have generally the same radial length and transverse thickness.

10. The structure of claim 8 wherein: said annular member holding parts of the suturing member includes a heat shrunk collar engaging a portion of the cover to hold the suturing member on said outside wall of the base.

* * * * *